United States Patent
Anger et al.

(10) Patent No.: US 11,224,712 B2
(45) Date of Patent: Jan. 18, 2022

(54) MULTIFUNCTONAL APPLICATOR WHICH CAN BE USED IN A MOBILE MANNER FOR MOBILE USE

(71) Applicant: TNI MEDICAL AG, Würzburg (DE)

(72) Inventors: Ewald Anger, Eibelstadt (DE); Dieter Klaus, Maulburg (DE); Peter Urban, Freiburg (DE)

(73) Assignee: TNI MEDICAL AG, Würzburg (DE)

( * ) Notice: Subject to any disclaimer, the term of this patent is extended or adjusted under 35 U.S.C. 154(b) by 913 days.

(21) Appl. No.: 15/524,340

(22) PCT Filed: Nov. 13, 2014

(86) PCT No.: PCT/EP2014/074457
§ 371 (c)(1),
(2) Date: May 4, 2017

(87) PCT Pub. No.: WO2016/074722
PCT Pub. Date: May 19, 2016

(65) Prior Publication Data
US 2017/0312471 A1  Nov. 2, 2017

(51) Int. Cl.
*A61M 16/08* (2006.01)
*A61M 16/06* (2006.01)
(Continued)

(52) U.S. Cl.
CPC .... *A61M 16/0833* (2014.02); *A61M 16/0057* (2013.01); *A61M 16/0096* (2013.01);
(Continued)

(58) Field of Classification Search
CPC .......... A61M 16/0057; A61M 16/0096; A61M 16/0666; A61M 16/0816; A61M 16/0833;
(Continued)

(56) References Cited

U.S. PATENT DOCUMENTS 4,004,603 A * 1/1977 Jones ............... A61M 16/20
                                                       128/205.24
4,919,127 A * 4/1990 Pell ................ A61M 16/0463
                                                       128/207.14
(Continued)

FOREIGN PATENT DOCUMENTS

CN    201658727 U    12/2010
DE       238349        12/1909
(Continued)

OTHER PUBLICATIONS

PCT English Language Translation of the International Preliminary Report on Patentability, PCT/EP2014/074457, dated May 26, 2017.
(Continued)

*Primary Examiner* — Victoria Murphy
(74) *Attorney, Agent, or Firm* — Quarles & Brady LLP

(57) ABSTRACT

The invention relates to a multifunctional applicator 6 for mobile use having an applicator plug 7, a supply tube 8, a Y-piece 9, fork tubes 10 and a nose piece 11 with prongs 12, wherein the applicator plug 7 comprises a pressure chamber 21 that has a humidifier interface 17 for connection with a high flow therapy device 1, an oxygen supply port 13 having an opening diameter of at least 1 mm, and a therapy air supply port 14 for the supply tube 8, the humidifier interface 17 and the oxygen supply port 13 within the pressure chamber 21 are both in fluid communication with an upper and a lower valve seat 23, 25 that are provided with a seal 22 and a valve body 24 being movable between said valve seats 23, 25 and said valve body 24 being subjected to a force by a helical compression spring 26 from the direction of the oxygen supply port 13 and on the other hand being pushed against the upper valve seat 25 by an actuating element 28 of the high flow therapy device 1 when the
(Continued)

applicator plug 7 is locked in place on the high flow therapy device 1.

14 Claims, 9 Drawing Sheets

(51) Int. Cl.
*A61M 16/10* (2006.01)
*A61M 16/00* (2006.01)
*A61M 16/16* (2006.01)
*A61M 16/20* (2006.01)
*A61M 39/24* (2006.01)

(52) U.S. Cl.
CPC .... *A61M 16/0666* (2013.01); *A61M 16/0816* (2013.01); *A61M 16/1005* (2014.02); *A61M 16/1095* (2014.02); *A61M 16/16* (2013.01); *A61M 16/208* (2013.01); *A61M 2039/248* (2013.01); *A61M 2039/2486* (2013.01); *A61M 2202/0208* (2013.01); *A61M 2205/0238* (2013.01); *A61M 2205/3561* (2013.01); *A61M 2205/52* (2013.01); *A61M 2205/8206* (2013.01); *A61M 2205/8237* (2013.01); *A61M 2205/8262* (2013.01); *A61M 2209/086* (2013.01)

(58) Field of Classification Search
CPC .......... A61M 16/1005; A61M 16/1095; A61M 16/16; A61M 16/208; A61M 2039/248; A61M 2039/2486; A61M 2202/0208; A61M 2205/0238; A61M 2205/3561; A61M 2205/52; A61M 2205/8206; A61M 2205/8237; A61M 2205/8262; A61M 2209/086; A61M 2230/205; A61M 16/20; A61M 16/08; A61M 16/209; A61M 2205/12; A61M 2205/50; A61M 16/0003; A61M 16/0672; A61M 16/0875; A61M 2205/3331; A61M 16/00; A61M 16/1055; A61M 2205/0205; A61M 2205/3341; A61M 39/22; A61M 2021/0066; A61M 16/145; A61M 16/142; A61M 11/041; A61M 11/04; A61M 2037/0038; A61M 2202/0241; F04C 28/24; A61J 11/0005; A62B 9/00; B65D 83/54; F16K 15/021; G06F 19/3456; G06F 19/3462; G08B 25/08; G16H 40/63; A61P 23/00; A61P 23/02; F17C 2201/0171; F17C 2201/032; F17C 2201/06; F17C 2203/0358; F17C 2203/0697; F17C 2205/2109; F17C 2227/00; F17C 2227/03; F17C 2227/0302; F17C 2227/0304; F17C 2227/0323; F17C 2227/0376; F17C 2227/0379; F17C 2227/0381; F17C 2270/02; F17C 2270/025; Y10T 137/4673; Y10T 137/479; Y10T 428/12042; Y10T 428/12049; Y10T 428/12056; Y10T 428/131; Y10T 428/1314
See application file for complete search history.

(56) References Cited

U.S. PATENT DOCUMENTS

| | | | |
|---|---|---|---|
| 6,119,291 A * | 9/2000 | Osborne | A61G 7/018 5/600 |
| 6,155,986 A * | 12/2000 | Brydon | A61B 5/087 128/911 |
| 6,158,430 A | 12/2000 | Pfeiffer et al. | |
| 8,230,859 B1 * | 7/2012 | Voege | A61M 16/0666 128/201.21 |
| 2002/0096174 A1 * | 7/2002 | Hill | A61M 16/10 128/205.11 |
| 2004/0167482 A1 * | 8/2004 | Watson | A61M 1/0001 604/317 |
| 2005/0121033 A1 * | 6/2005 | Starr | A61M 16/024 128/204.18 |
| 2005/0161043 A1 | 7/2005 | Whitley et al. | |
| 2007/0135757 A1 * | 6/2007 | Acker | A61M 16/0666 604/26 |
| 2007/0283957 A1 | 12/2007 | Schobel (nee Bauer) et al. | |
| 2008/0149096 A1 * | 6/2008 | Power | A61M 15/0085 128/200.14 |
| 2009/0025723 A1 * | 1/2009 | Schobel | A61M 16/0666 128/204.17 |

FOREIGN PATENT DOCUMENTS

| | | |
|---|---|---|
| DE | 10205955 A1 | 8/2003 |
| DE | 102005000922 A1 | 7/2006 |
| TW | 446565 B | 7/2001 |
| WO | 0055072 A2 | 9/2000 |
| WO | 2008060295 A2 | 5/2008 |
| WO | 2013089714 A1 | 6/2013 |

OTHER PUBLICATIONS

PCT International Search Report, PCT/EP2014/074457, dated Jul. 14, 2015.
Taiwan Patent Office, First Office Action and Search Report, Application No. 104132026, dated Oct. 13, 2016.

* cited by examiner

MULTIFUNCTONAL APPLICATOR WHICH CAN BE USED IN A MOBILE MANNER FOR MOBILE USE

CROSS-REFERENCE TO RELATED APPLICATIONS

This application represents the national stage entry of PCT International Application No. PCT/EP2014/074457 filed Nov. 13, 2014, the contents of which is hereby incorporated herein by reference for all purposes.

STATE OF THE ART

Nasal insufflation systems for high flow therapy are known from WO 2008/060 295 A2, for example. Filtered air is sucked in by a blower, is compressed and enriched with oxygen, and said mixture is atomized in a heated humidifier and administered to the patient as therapy air into the nostrils by means of an applicator, provided that the patient is an adult. With children, a mouth piece is additionally required.

In the nasal insufflation system known from the above-mentioned published patent application, the therapy air is enriched with oxygen in a high flow therapy device by means of a microprocessor-controlled valve. The ambient air, which is suctioned through an air inlet and filtered in the high flow therapy device, is thus actively mixed with pure oxygen, which is supplied through a separate supply port on the high flow therapy device. Apart from the oxygen content, the microprocessor controls other parameters of the supplied therapy air, such as gas pressure, gas flow, carbon dioxide content, temperature and humidity. The applicator is directly and permanently connected to the high flow therapy device when the nasal insufflation system is in use.

From DE 10 2005 000 922 A1, an applicator is known that comprises an applicator plug, a supply tube, a Y-piece, fork tubes and a nose piece with prongs. The applicator plug itself has electrical and pneumatic plug components. The present invention is based on an applicator of this kind.

DE 102 05 955 A1 discloses a method and a device for providing breathing gas, an oxygen generator performing an electrolytic separation of water into hydrogen and oxygen and the generated oxygen being compressed and fed into a pressurized gas cylinder. The oxygen generator both fills the pressurized gas cylinder and supplies breathing gas for an oxygen cannula by means of a control device provided with a distributor, which determines conduction of the breathing gas towards the oxygen cannula and/or toward the pressurized gas cylinder as a function of respective control specifications. The document also discloses that a patient can optionally form a connection with an oxygen generator or with a pressurized gas cylinder via a consumption control as a connection element. In order to provide the patient with a relatively large range of motion in their home or in another room, a longer connecting tube to the oxygen cannula is proposed.

From DE 238 349 A, a breathing device for entering rooms with non-breathable atmosphere is known, wherein the air supply from a permanently connected portable oxygen tank to the respiratory system can be opened or shut via a three-way valve that can be adjusted by means of a hand lever, and, at the same time, a tube, which otherwise supplies external air, is decoupled and coupled by means of a coupling part that is attached to the cock plug of the three-way valve.

A ventilator system for performing CPAP or oxygen therapy intended in particular for hospitals is known from U.S. Pat. No. 6,158,430 A. It consists of one or multiple portable ventilator units that can be operated by means of associated interfaces at docking stations installed in different places or wards. The docking stations themselves are connected to a central gas supply of the hospital in order to provide the oxygen supply for the ventilator units. Additionally, individual gas cylinders can also be connected directly to a docking station.

From WO 2013/089714 A1, a hybrid self-rescue equipment is known that enables individuals to move in harsh environments, such as mines, tunnels or tanks with contaminated air. All necessary components, such as a breathing tube, a mouth piece, a breathing mask, nose clips, goggles etc. are housed in a portable housing. Furthermore, the self-rescue equipment has a valve housing with multiple ports, to which breathing tubes or dust filters can be optionally connected.

Since applicators as the ones known from DE 10 2005 000 922 A1, for example, have to be connected to the high flow device at all times in order to supply the patient with air and since the high flow therapy device is not portable at will because of its physical size and weight, the patient is bound to the high flow therapy device and thus immobile. Also, the supply tube cannot have any length to provide some freedom of movement to the patient because the parameters of the supplied therapy air, in particular the flow and pressure properties, cannot be ensured at the nose piece with the set parameters as they are generated by the high flow therapy device because said parameters change on their way from the high flow therapy device to the nose piece due to external influences.

The lack of mobility of the patient is a significant disadvantage. The patient is unable to briefly move shorter distances without gas supply and thus breathing support.

Underlying Problem and Solution

The underlying object of the present invention is to remedy this shortcoming, to simultaneously achieve maximum mobility and flexibility and to furthermore allow a supply with oxygen or therapy air. Said object is attained by a multifunctional applicator for mobile use having an applicator plug, a supply tube, a Y-piece, fork tubes, and a nose piece with prongs, wherein the applicator plug comprises a pressure chamber having a humidifier interface for connection with a high flow therapy device, an oxygen supply port having an opening diameter of at least 1 mm, and a therapy air supply port for the supply tube, wherein the humidifier interface and the oxygen supply port both have an upper and a lower valve seat provided with a seal and a valve body being movable between the upper and lower valve seats, the valve body being forced against the lower valve seat by a helical compression spring opening the oxygen supply port when the applicator plug is removed and forced against the upper valve seat by an actuating element of the high flow therapy device closing the oxygen supply port and preventing oxygen flow when the applicator plug is locked in place on the high flow therapy device. Additional advantages of the invention are indicated in the dependent claims.

Gained Advantages

The multifunctional applicator for mobile use with its advantageous construction of the applicator plug allows, on the one hand, a continuous supply with conditioned therapy air (TNI) provided by the high flow therapy device and, on the other hand, ensures the supply with oxygen (LTOT) or with therapy air when the patient removes the applicator plug from the high flow therapy device in order to, for example, go to the bathroom, kitchen etc. by switching automatically.

On these walks, the patient is supplied by an easy-to-handle portable oxygen or therapy air source and the oxygen or therapy air support is thus ensured without interruption. To the patient, this means significant gains in quality of life; they no longer have to worry about a drop in or failure of their breathing support and are thus protected from a possible life-threatening situation.

Moreover, the patient is supposed to be supplied with a constant volume flow of therapy air in both their nostrils when the applicator is plugged on because only then the dead space can be reliably flushed. To this end, the parameters of the therapy air are measured close to the patient and said parameters are predominantly controlled in the high flow therapy device in such a manner that the volume flow is kept constant at the outlet openings of the prongs of the nasal cannula. This is achieved by advantageous measures that are explained in more detail in the description.

The design of the valve body as a sphere allows a simple structure in terms of the valve seats and their seals in order to ensure the valve function.

If, in contrast, the valve body is realized as a cylinder piston the advantages common for this embodiment are achieved, such as improved and easier sealing.

Since the electronic components present in the applicator have to be supplied with energy, contacts for a power supply and/or for signal and data lines are already present in the applicator, and no additional external connection lines are required.

According to patent claim 5, in the Y-piece, a function unit is advantageously installed that comprises a directional valve, transmitters and receivers and an electronic processing unit. These components are supplied with energy in a simple manner via heating wires in the supply tube or by batteries or rechargeable batteries.

The applicator plug itself can be equipped with a programmable microprocessor whose memory contains patient data as well as parameter indications of the individually required therapy air and service data that are needed for evaluation by the control function in the high flow therapy device. When changing the therapy devices, the patient can thus be supplied with the same therapy air associated to them without having to reset the device because the set values can be carried over from the applicator plug.

In order to be able to more individually address anatomic asymmetries, the Y-piece is arranged no closer than 5 mm to the prongs.

The use of antibacterially coated materials protects the patient from infections.

Furthermore, it is advantageous that therapy air can also be supplied at the oxygen supply port instead of oxygen.

DESCRIPTION OF AN EMBODIMENT EXAMPLE

Figure 1:
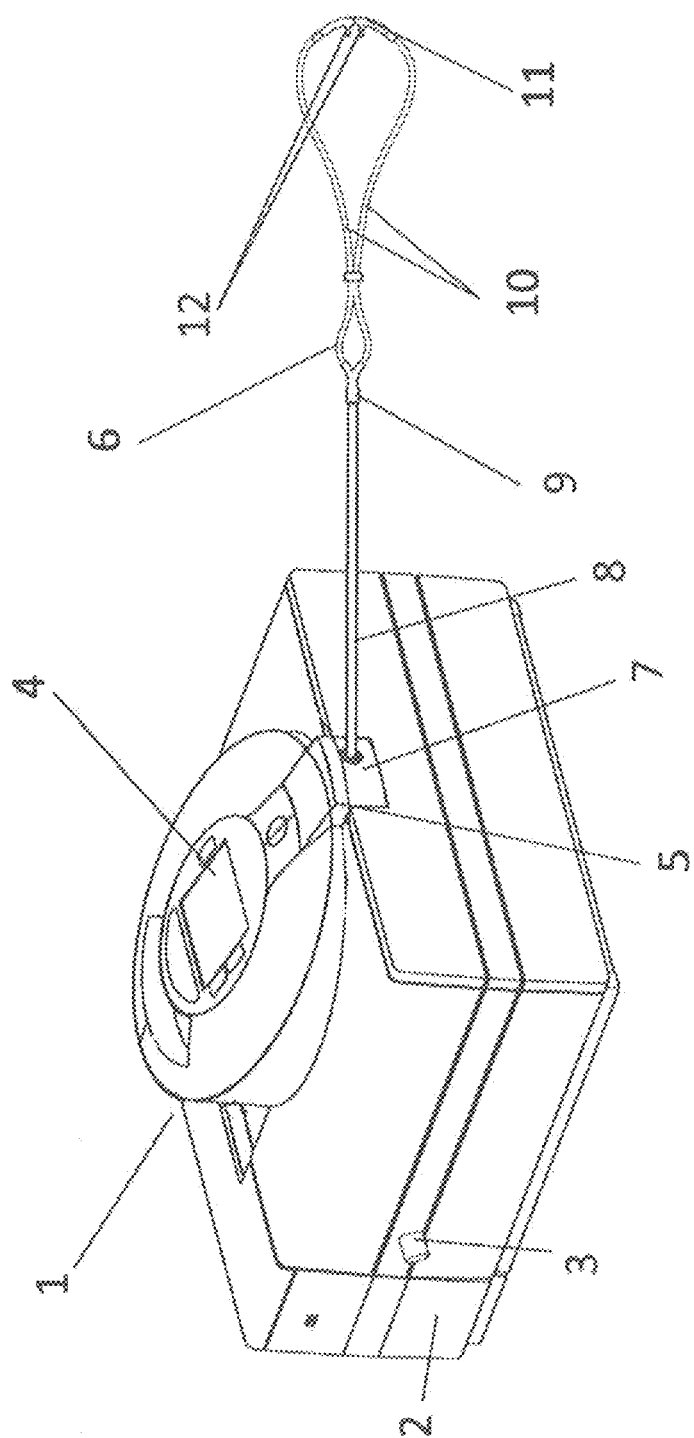
FIG. 1 shows a nasal insufflation system according to the state of the art.

FIG. 1 shows a nasal insufflation system consisting of a high flow therapy device 1 and an applicator 6 according to the state of the art. The inlet for the ambient air 2, the port for the oxygen supply 3, the operating and displaying device 4 and the port 5 for the applicator 5 at the outlet for the therapy air are visible on the high flow therapy device 1. The applicator 6 basically consists at least of one applicator plug 7, a supply tube 8, a Y-piece 9, fork tubes 10 and a nose piece 11 with prongs 12.

Figure 2:
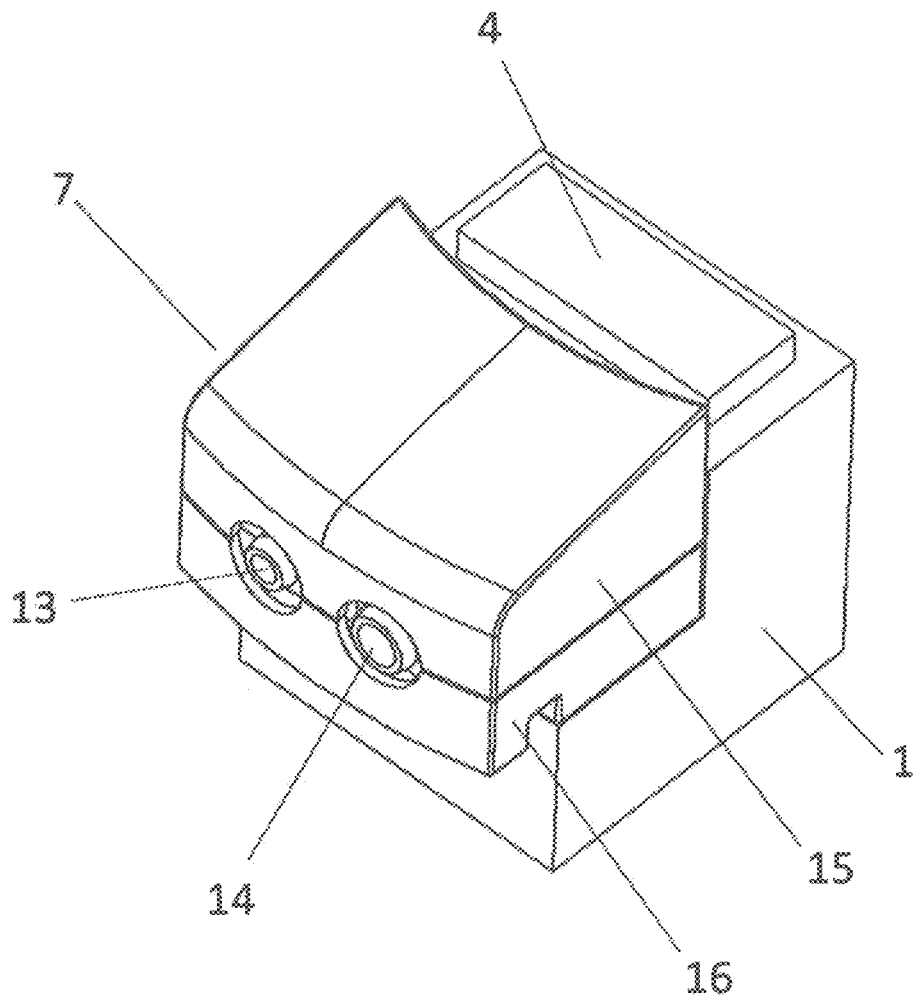
FIG. 2 shows an applicator plug according to the invention connected to a high flow therapy device.

The multifunctional applicator 6 for mobile use according to the invention is equipped with an applicator plug 7, which, as shown in FIG. 2, can be mounted on top of the high flow therapy device 1, and has an oxygen supply port 13 and a therapy air supply port 14 for the supply tube 8, which is not illustrated in this Figure. The applicator plug 7 consists at least of a top part 15 and a bottom part 16.

Figure 3:
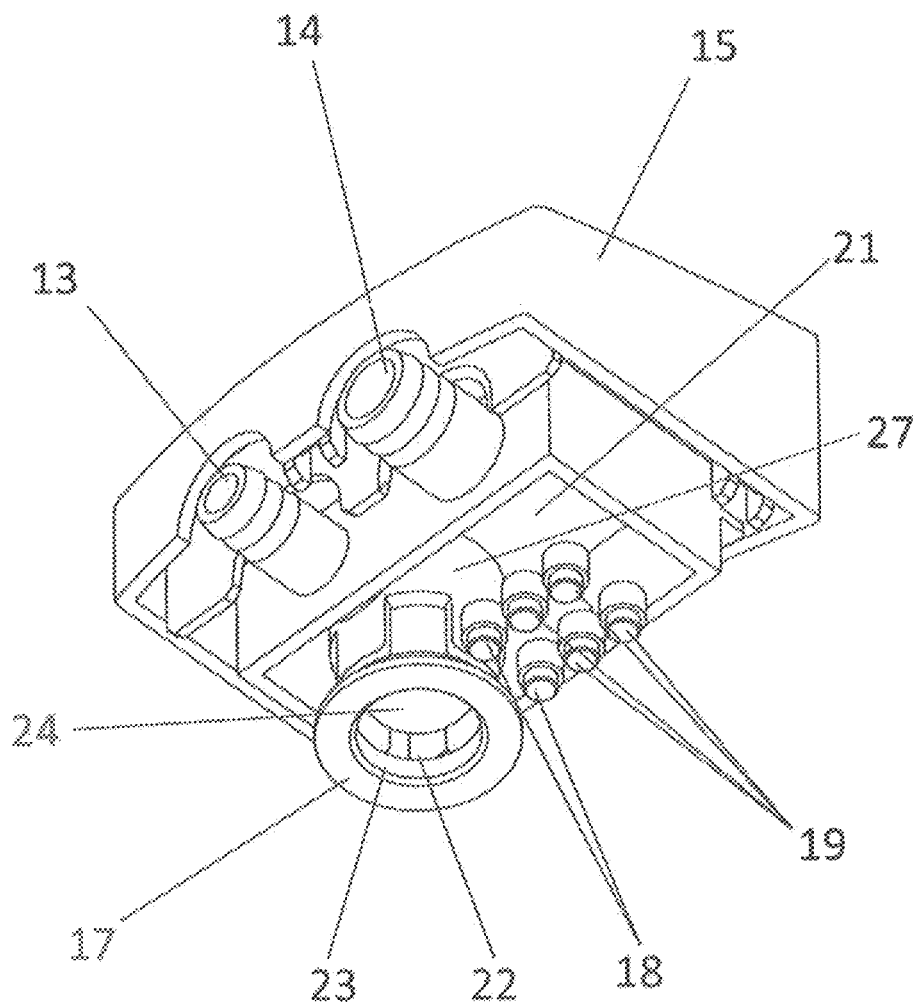
FIG. 3 shows a top part of the applicator plug according to the invention.

FIG. 3 shows the top part 15 of the applicator plug 7 from below in a partial view including a humidifier interface 17 through which the applicator plug 7 is supplied with conditioned therapy air from the high flow therapy device 1. Furthermore, a lower valve seat 23 with its seal 22 and a valve body 24 above it are illustrated, said valve body 24 being mobile in a straight manner in a guide 27. Said guide 27 is arranged in a pressure chamber 21. Additionally, contacts 18/19 for the power supply and for signal and/or data lines are illustrated.

Figure 4:
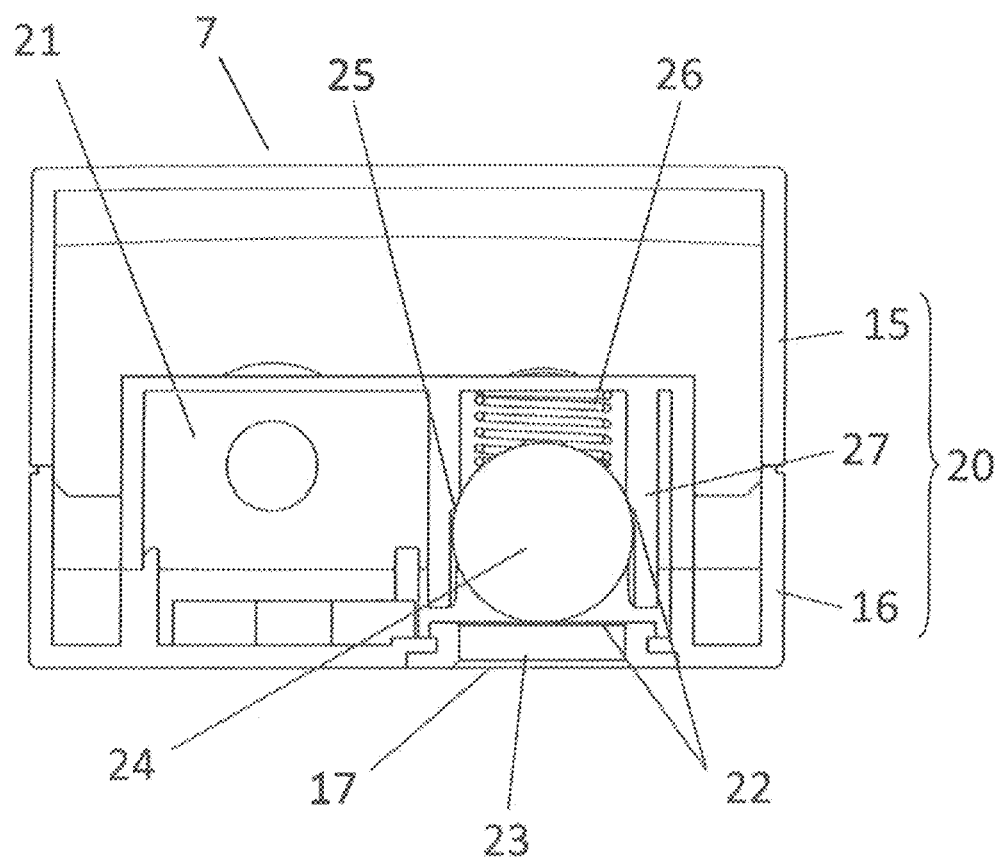
FIG. 4 shows a vertical section through the applicator plug according to the invention.

A vertical section through the applicator plug 7, FIG. 4, shows the housing 20 of the applicator plug 7, which consists of a top part 15 and a bottom part 16 and comprises the pressure chamber 21, into which therapy air can flow from below from the high flow therapy device 1 via the humidifier interface 17. At its upper end, said humidifier interface 17 has the lower valve seat 23, which is equipped with the seal 22 and on which the valve body 24 (e.g., a sphere as in this case or a cylindrical valve piston) rests when the applicator plug 7 is not placed on the high flow therapy device 1. Above the valve body 24, there is another, upper valve seat 25, which is also equipped with a seal 22 and which can form a connection with the oxygen supply port 13. A helical compression spring 26 is visible as well, whose spring force acts on the valve body 24 and thus pushes said valve body 24 against the seal 22 of the lower valve seat 23 of the humidifier interface 17. In this way, the humidifier interface 17 is reliably sealed when the applicator plug 7 is removed from the high flow therapy device 1.

Figure 5:
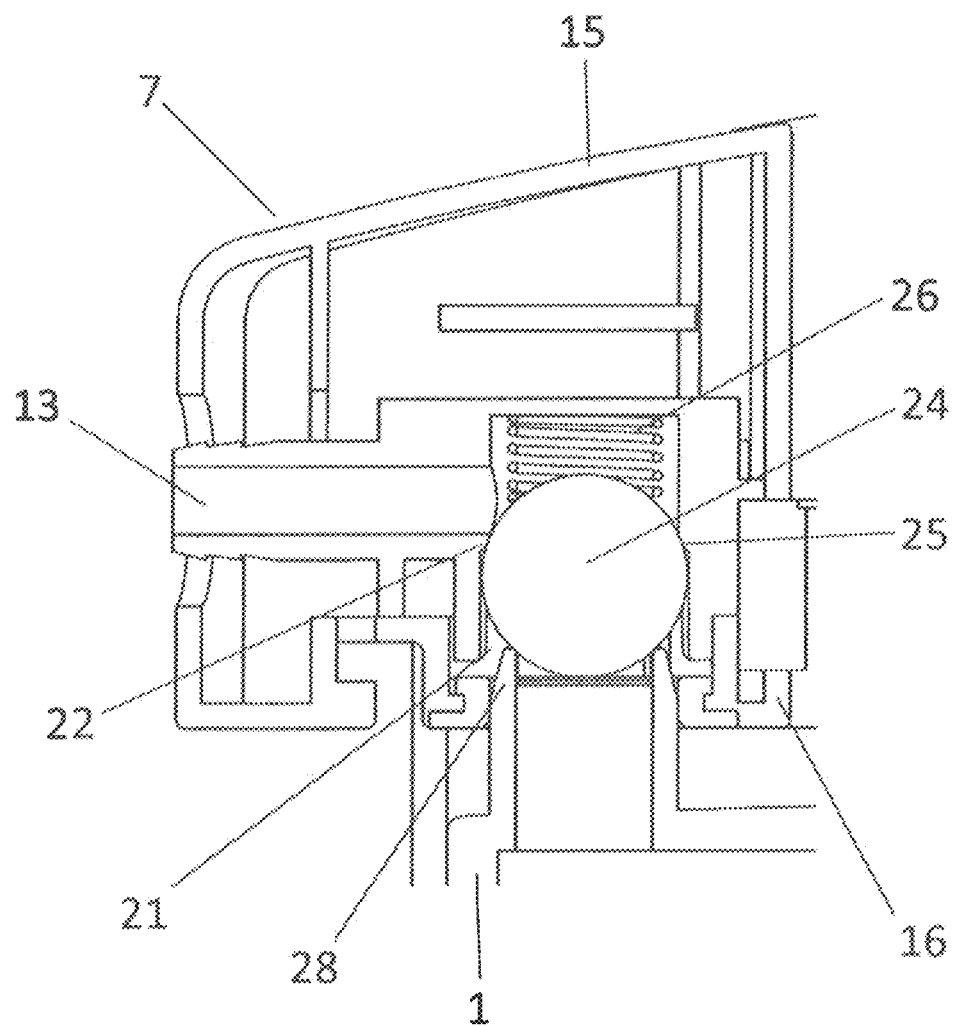
FIG. 5 shows a vertical section through the applicator plug according to the invention including an actuating element in the plane of the oxygen supply port.

When the applicator plug 7 is locked in place on the high flow therapy device 1 by means of a latching or locking connection, as shown in FIG. 5, the valve body 24 is pushed upward against the seal 22 of the upper valve seat 25 by an actuating element 28, which is fixed thereto so as to be immobile. Thus, no oxygen can flow into the pressure chamber 21 via the oxygen supply port 13. This ensures that the therapy air provided by the high flow therapy device 1 flows into the pressure chamber 21 and further via the therapy air supply port 14, which cannot be illustrated in this section plane, toward the supply tube 8. This flow path is the usual case.

Figure 6:
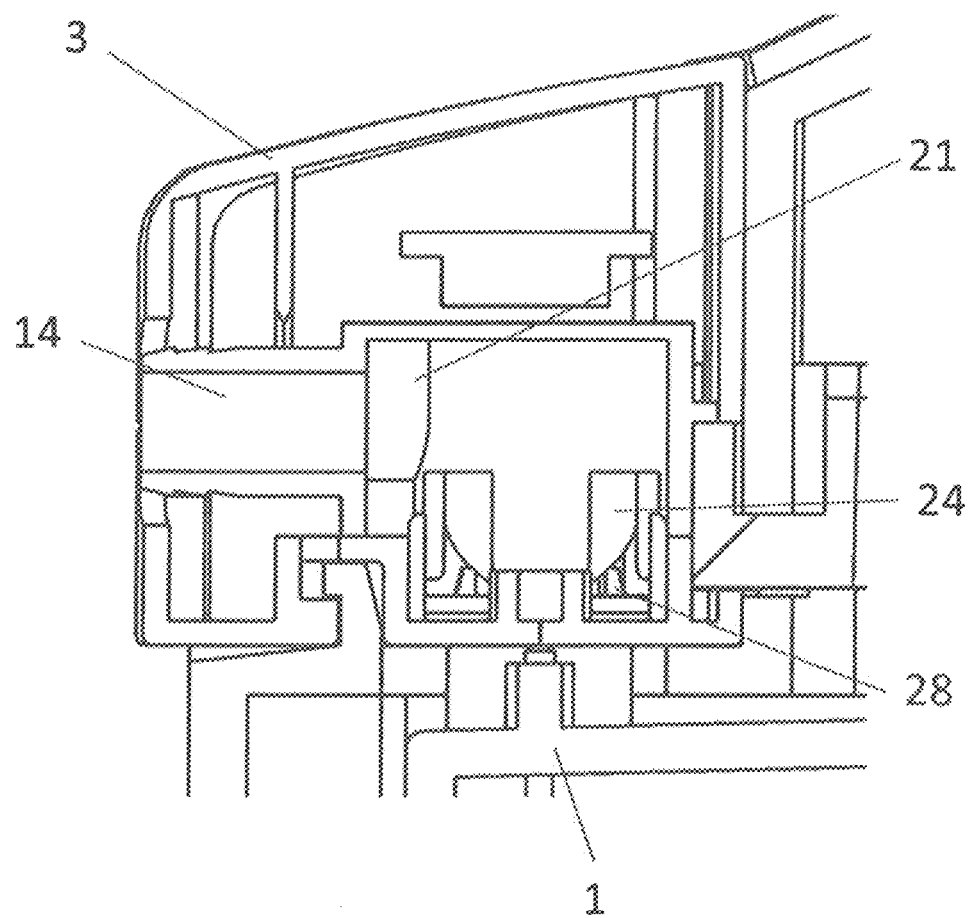
FIG. 6 shows a vertical section through the top part of the applicator plug according to the invention in the plane of the therapy air supply port.

FIG. 6 shows a vertical section through the applicator plug 7 of the multifunctional applicator 6 for mobile use in the plane of the therapy air supply port 14 for the supply tube 8 (not illustrated). Said therapy air supply port 14 forms the connection between the pressure chamber 21 and the supply tube 8. Said connection is always open when the applicator plug 7 is placed on the high flow therapy device 1 and tightly latched or locked because the actuating element 28 lifts the valve body 24 from the seal 22, shown in FIG. 5, of the valve seat 23 and then always supplies the pressure chamber 21 with therapy air.

If the patient wishes to be mobile for a foreseeable time, then at the latest the portable oxygen cylinder, whose filling level is monitored, is to be connected to the oxygen supply port 13 if that has not happened yet. When the applicator plug 7 is now removed from the high flow therapy device 1, the actuating element 28 no longer acts on the valve body 24. The force of the helical compression spring 26 now pushes the valve body 24 against the seal 22 of the lower valve seat 23 and the valve body 24 closes the lower valve seat 23. Oxygen then flows via the oxygen supply port 13 into the pressure chamber 21 and further via the therapy air supply port 14 into the supply tube 8. The multifunctional applicator 6 for mobile use with a small, easy-to-handle oxygen or therapy air source can be handled effortlessly and comfortably by the patient when moving about and thus allows the mobile option of movement in the first place while maintaining the oxygen or therapy air supply without the high flow therapy device 1. The uninterrupted supply with oxygen or therapy air is thus reliably ensured during movement as well, which would be impossible without the afore-described valve structure according to the invention and its function.

Figure 7:
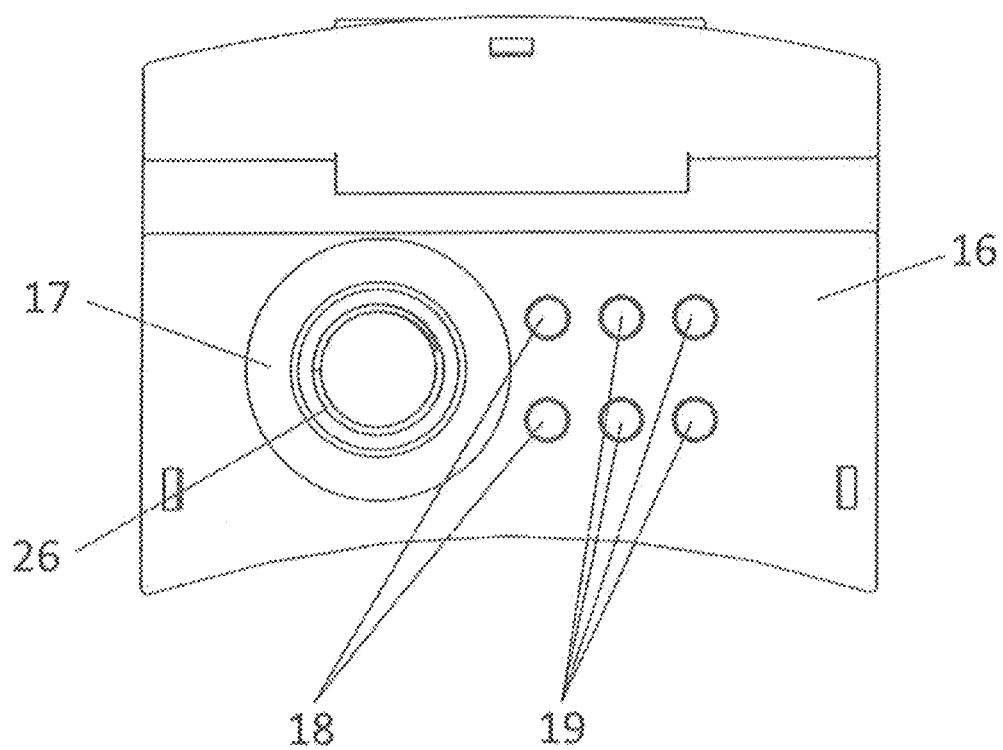
FIG. 7 shows a bottom view of the applicator plug according to the invention.

The view of the applicator plug 7 from below (plug side toward the high flow device) in FIG. 7 shows the helical compression spring 26 and the contacts 18 and 19 for the power supply and/or the signal and/or data lines (e.g., for data line 32, FIG. 8) in addition to the humidifier interface 17 because the valve body 24 is not illustrated here. Said contacts correspond to corresponding contacts of the high flow therapy device 1.

In addition to the function of mobile usability, the multifunctional applicator 6 for mobile use according to the invention allows monitoring functions (such as use time, temperature, service intervals etc.), which will be described in more detail in view of FIGS. 8 and 9.

Figure 8:
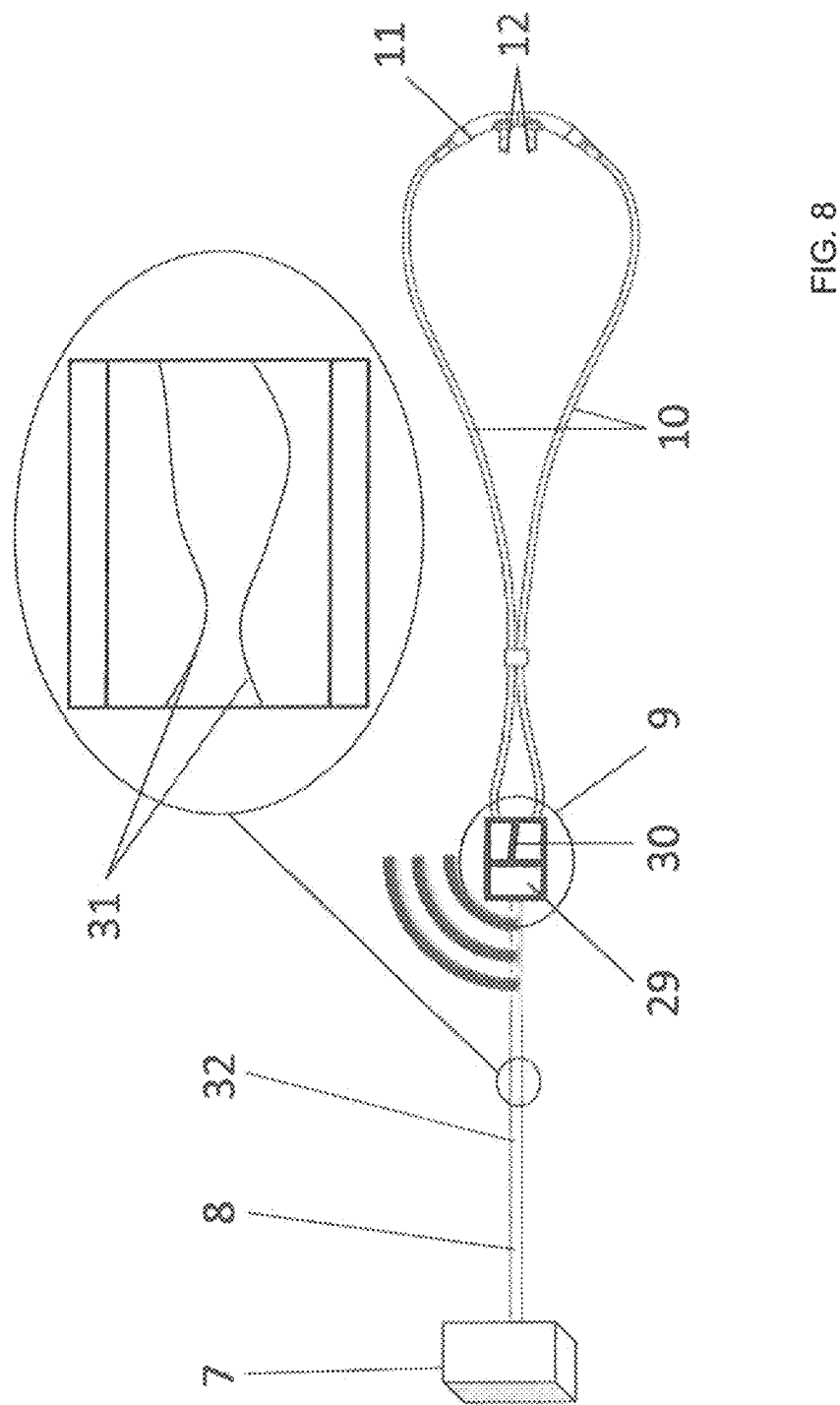
FIG. 8 shows an applicator according to the invention including a function unit.

If needed, the Y-piece 9, which conducts the therapy air, can be equipped with a function unit 29, as illustrated in FIG. 8. Said function unit 29 comprises sensors 33 (FIG. 9), which measure volume flow, humidity, temperature etc, for example. The measured data are transmitted to the applicator plug 7 by way of a data line 32 in the supply tube 8 and on to the high flow therapy device 1 via the contacts 19. Alternatively to the data line 32, the function unit 29 has transmitters and receivers for data transmission or transmits said data directly via the heating line. Said transmitters and receivers communicate with the corresponding receiver and transmitter either in the applicator plug 7 or in the high flow therapy device 1. If transmitters and receivers are installed in the applicator plug 7, the data are transmitted to the high flow therapy device 1 by way of the contacts 19 so that the high flow therapy device 1 can optimize the parameters of the therapy air. The transmitters and receivers in the function unit 29 can be supplied with energy by means of batteries or rechargeable batteries. Power supply via the heating wires 31, which run in the supply tube 8 and transmit the necessary energy, is possible as well. Also, the rechargeable batteries can be charged via the heating wires 31 (see enlarged section in FIG. 8).

Figure 9:
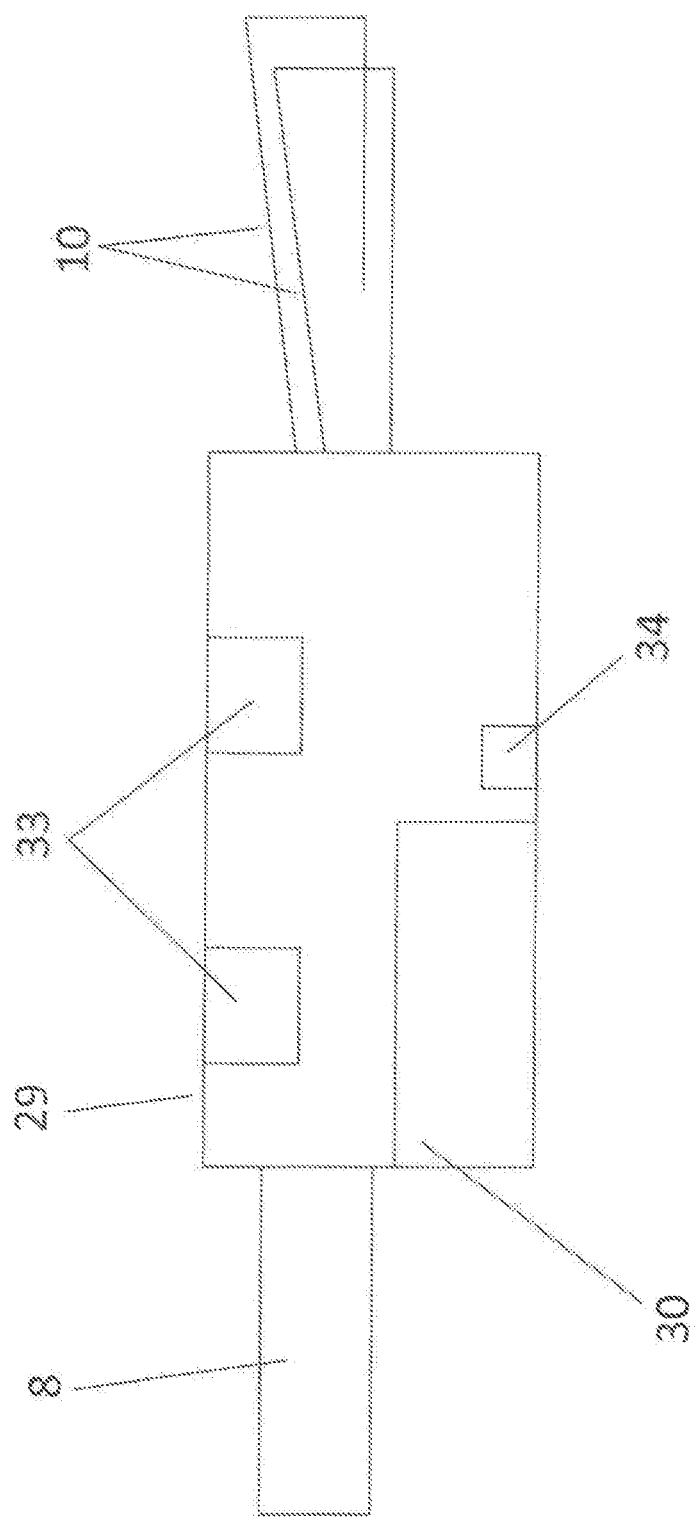
FIG. 9 shows details of the function unit.

To implement this function, the function unit 29, as shown in FIG. 9, has sensors 33 for measuring the parameters of the therapy air flowing by and an electronic processing unit 34, which transmits the measured data.

Apart from the mentioned sensors 33, a directional valve 30 may be provided in the function unit 29, said directional valve 30 guiding the therapy air to the fork tubes 10 in different ways. In this manner, the constant volume flow is ensured in the area of the prongs 12 at their outlet openings by way of the fork tubes 10 alternatively as a function of suitable sensors. The variable resistance of the respiratory ducts of the patient through the nostrils is thus taken into account.

The applicator plug 7 can further have a programmable microprocessor, in which service data, the data and the parameters of the patient using the multifunctional applicator 6 for mobile use are stored. Said data may be necessary for individual control of the high flow therapy device 1 because correct conditioning of the therapy air can be set in this way. If the patient changes the previously used high flow therapy device 1 with their multifunctional applicator 6 for mobile use, the high flow therapy device 1 automatically resets itself and the patient instantaneously receives conditioned therapy air with the parameters necessary and defined for them, which means that the patient is independent from the chosen high flow therapy device 1 in this regard. This is conditioned on the fact that the high flow therapy device 1 itself has a corresponding controller that can process the data from the microprocessor in the applicator plug 7.

The patient's data also include the applicator-specific properties, for example, such as flow limitation in an applicator for children, identification of the applicator type, operating hours and running times etc.

Alternatively to the directional valve 30 in the function unit 29, a controlled directional valve may be located in the nose piece 11 between the prongs 12 in order to keep the volume flow constant at the respective outlet openings of the prongs 12. Said control is implemented by way of the same technical solution as in function unit 29. Also, the outlet cross-sections of the prongs 12 may be shaped asymmetrically. For instance, different cross-section surfaces and/or cross-section shapes of the outlet openings of the prongs 12 in the nostril are furthermore conceivable.

The inner diameter of the oxygen supply port 13 is at least 1 mm. Preferably, the inner diameter of the oxygen supply port 13 is between 1 and 10 mm.

The inner diameter of the therapy air supply port 14 is at least 2 mm. Preferably, the inner diameter of the therapy air supply port 14 is between 2 and 25 mm.

The object of any of the afore-described measures is to provide a constant volume flow at the respective outlet openings of the prongs 12 while all necessary parameters are taken into account.

LIST OF REFERENCE SIGNS

1 high flow therapy device
2 inlet for ambient air
3 port for oxygen supply
4 operating and displaying device of the high flow therapy device
5 port for applicator plug 6 applicator
7 applicator plug
8 supply tube
9 Y-piece
10 fork tubes
11 nose piece
12 prongs
13 oxygen supply port
14 therapy air supply port
15 top part of the applicator plug
16 bottom part of the applicator plug
17 humidifier interface
18 contacts for power supply
19 contacts for signal and/or data lines
20 housing of the applicator plug
21 pressure chamber
22 seal
23 lower valve seat
24 valve body
25 upper valve seat
26 helical compression spring
27 guide for valve body
28 actuating element
29 function unit
30 directional valve
31 heating wires
32 data line
33 sensors
34 electronic processing unit

The invention claimed is:

1. A multifunctional applicator for mobile use comprising:
an applicator plug,
a supply tube,
a Y-piece,
fork tubes, and
a nose piece with prongs;
wherein the applicator plug comprises:
a pressure chamber having a humidifier interface for connection with a high flow therapy device,
an oxygen supply port having an opening diameter of at least 1 mm,
a therapy air supply port for the supply tube,
a valve body, and
a helical compression spring;
wherein the humidifier interface and the oxygen supply port are both in fluid communication with an upper valve seat and a lower valve seat with a seal;
the valve body being movable between the upper valve seat and the lower valve seat;
wherein the helical compression spring is configured to force the valve body against the lower valve seat, thereby opening the oxygen supply port when the applicator plug is removed from the high flow therapy device;
the valve body configured to be forced against the upper valve seat by an actuating element of the high flow therapy device, thereby closing the oxygen supply port and preventing oxygen flow when the applicator plug is locked in place on the high flow therapy device.

2. The multifunctional applicator for mobile use according to claim 1, wherein the valve body is a sphere.

3. The multifunctional applicator for mobile use according to claim 1, wherein the valve body is a cylinder piston.

4. The multifunctional applicator for mobile use according to claim 1, wherein the applicator plug has contacts for a power supply and/or for signal and/or data lines.

5. The multifunctional applicator for mobile use according to claim 1, wherein a function unit with sensors is integrated in the Y-piece.

6. The multifunctional applicator for mobile use according to claim 1, wherein a function unit with a directional valve is integrated in the Y-piece.

7. The multifunctional applicator for mobile use according to claim 1, wherein a function unit with transmitters and receivers is integrated in the Y-piece, the transmitters and receivers configured to communicate with transmitters and receivers either in the applicator plug or in the high flow therapy device.

8. The multifunctional applicator for mobile use according to claim 1, wherein a function unit with an electronic processing unit is integrated in the Y-piece.

9. The multifunctional applicator for mobile use according to claim 8, wherein the electronic processing unit is supplied with energy via heating wires in the supply tube or by a battery or a rechargeable battery.

10. The multifunctional applicator for mobile use according to claim 1, wherein the applicator plug has a programmable microprocessor.

11. The multifunctional applicator for mobile use according to claim 10, wherein service data, patient data and therapy parameters individually required by the patient are stored in a memory of the programmable microprocessor.

12. The multifunctional applicator for mobile use according to claim 1, wherein the Y-piece is located at least 5 mm from the prongs.

13. The multifunctional applicator for mobile use according to claim 1, further comprising an antibacterial coating.

14. The multifunctional applicator for mobile use according to claim 1, wherein in mobile use, an oxygen or therapy air source is connected to the oxygen supply port.

* * * * *